United States Patent
Day

[19]

[11] Patent Number: 6,076,660

[45] Date of Patent: Jun. 20, 2000

[54] VIAL FOR DENTAL IMPLANT DELIVERY SYSTEM

[75] Inventor: Thomas H. Day, San Diego, Calif.

[73] Assignee: Sulzer Calcitek Inc., Carlsbad, Calif.

[21] Appl. No.: 09/019,159

[22] Filed: Feb. 5, 1998

[51] Int. Cl.[7] .................................................. A61B 19/02
[52] U.S. Cl. ...................... 206/63.5; 206/373; 206/369; 220/283; 220/838
[58] Field of Search ................... 206/63.5, 369, 206/373, 570; 220/281, 283, 837, 839, 375, 757; 224/240, 236

[56] References Cited

U.S. PATENT DOCUMENTS

| | | |
|---|---|---|
| Re. 8,112 | 3/1878 | Frazier . |
| D. 351,904 | 10/1994 | Maze . |
| 394,376 | 12/1888 | Kelton . |
| 2,112,007 | 3/1938 | Adams . |
| 3,067,740 | 12/1962 | Haboush . |
| 3,488,779 | 1/1970 | Christensen . |
| 3,846,846 | 11/1974 | Fischer . |
| 3,990,438 | 11/1976 | Pritchard . |
| 4,027,392 | 6/1977 | Sawyer et al. . |
| 4,145,764 | 3/1979 | Suzuki et al. . |
| 4,177,562 | 12/1979 | Miller et al. . |
| 4,180,192 | 12/1979 | Breslau . |
| 4,234,309 | 11/1980 | Sellers . |
| 4,244,495 | 1/1981 | Lorscheid et al. ................. 222/153 |
| 4,259,072 | 3/1981 | Hirabayashi et al. . |
| 4,412,616 | 11/1983 | Williams ........................... 206/333 |
| 4,414,966 | 11/1983 | Stednitz . |
| 4,424,037 | 1/1984 | Ogino et al. . |
| 4,444,310 | 4/1984 | Odell . |
| 4,463,753 | 8/1984 | Gustilo . |
| 4,468,200 | 8/1984 | Munch . |
| 4,480,997 | 11/1984 | Deutsch et al. . |
| 4,484,570 | 11/1984 | Sutter et al. . |
| 4,495,664 | 1/1985 | Blanquaret . |
| 4,511,335 | 4/1985 | Tatum, Jr. . |
| 4,535,487 | 8/1985 | Esper et al. . |
| 4,537,185 | 8/1985 | Stednitz . |
| 4,553,942 | 11/1985 | Sutter . |
| 4,615,462 | 10/1986 | Sacherer et al. . |
| 4,668,191 | 5/1987 | Plischka . |
| 4,671,410 | 6/1987 | Hansson et al. . |
| 4,712,681 | 12/1987 | Branemark et al. . |
| 4,713,003 | 12/1987 | Symington et al. . |
| 4,713,004 | 12/1987 | Linkow et al. . |
| 4,713,219 | 12/1987 | Gerken et al. ...................... 422/102 |
| 4,717,018 | 1/1988 | Sacherer et al. . |
| 4,722,688 | 2/1988 | Lonca . |
| 4,722,733 | 2/1988 | Howson . |
| 4,738,623 | 4/1988 | Driskell . |
| 4,758,161 | 7/1988 | Niznick . |
| 4,763,788 | 8/1988 | Jorneus et al. . |
| 4,790,753 | 12/1988 | Fradera . |
| 4,793,808 | 12/1988 | Kirsch . |
| 4,795,056 | 1/1989 | Meyers .............................. 220/306 |

(List continued on next page.)

FOREIGN PATENT DOCUMENTS

| | | |
|---|---|---|
| 0312698 | 4/1998 | European Pat. Off. . |
| 30 43 336 | 6/1981 | Germany . |
| 1662545 | 7/1991 | U.S.S.R. . |
| 1727808 | 4/1992 | U.S.S.R. . |
| 1291470 | of 0000 | United Kingdom . |

OTHER PUBLICATIONS

U.S. Patent Application Ser. No. 08/6889,696 for Dental Implant Delivery System, filed on Aug. 16, 1996, Inventor Michael John Biggs.

*Primary Examiner*—Paul T. Sewell
*Assistant Examiner*—Nhan T. Lam
*Attorney, Agent, or Firm*—Philip S. Lyren; Kenneth S. Barrow

[57] ABSTRACT

A vial for a dental implant delivery system. The vial includes a clip and a lid that is permanently attached to the body of the vial. The lid disengages from the top of the vial when the body of the vial is squeezed.

7 Claims, 4 Drawing Sheets

6,076,660
Page 2

U.S. PATENT DOCUMENTS

| | | | |
|---|---|---|---|
| 4,826,434 | 5/1989 | Krueger . | |
| 4,851,008 | 7/1989 | Johnson . | |
| 4,854,872 | 8/1989 | Detsch . | |
| 4,856,648 | 8/1989 | Krueger . | |
| 4,856,994 | 8/1989 | Lazzara et al. . | |
| 4,863,383 | 9/1989 | Grafelmann . | |
| 4,878,915 | 11/1989 | Brantigan . | |
| 4,915,628 | 4/1990 | Linkow et al. . | |
| 4,915,629 | 4/1990 | Sellers . | |
| 4,927,363 | 5/1990 | Schneider . | |
| 4,932,868 | 6/1990 | Linkow et al. . | |
| 4,934,935 | 6/1990 | Edwards . | |
| 4,942,991 | 7/1990 | Lyons . | |
| 4,955,811 | 9/1990 | Lazzara et al. . | |
| 4,960,381 | 10/1990 | Niznick . | |
| 4,976,617 | 12/1990 | Carchidi . | |
| 4,978,007 | 12/1990 | Jacobs et al. . | |
| 4,978,350 | 12/1990 | Wagenknecht . | |
| 4,982,882 | 1/1991 | Gueret | 222/531 |
| 4,988,299 | 1/1991 | Branemark . | |
| 5,015,186 | 5/1991 | Detsch . | |
| 5,018,970 | 5/1991 | Stordahl . | |
| 5,026,280 | 6/1991 | Durr et al. . | |
| 5,026,285 | 6/1991 | Durr et al. . | |
| 5,030,095 | 7/1991 | Niznick . | |
| 5,030,096 | 7/1991 | Hurson et al. . | |
| 5,035,619 | 7/1991 | Daftary . | |
| 5,049,073 | 9/1991 | Lauks . | |
| 5,061,181 | 10/1991 | Niznick . | |
| 5,062,800 | 11/1991 | Niznick . | |
| 5,064,425 | 11/1991 | Branemark et al. . | |
| 5,069,336 | 12/1991 | Mauthe . | |
| 5,073,111 | 12/1991 | Daftary . | |
| 5,076,788 | 12/1991 | Niznick . | |
| 5,078,607 | 1/1992 | Niznick . | |
| 5,100,323 | 3/1992 | Friedman et al. . | |
| 5,106,300 | 4/1992 | Voitik . | |
| 5,117,976 | 6/1992 | Whitt et al. . | |
| 5,125,840 | 6/1992 | Durr et al. . | |
| 5,135,394 | 8/1992 | Hakamatsuka et al. . | |
| 5,145,372 | 9/1992 | Daftary et al. . | |
| 5,167,664 | 12/1992 | Hodorek . | |
| 5,174,482 | 12/1992 | Rogers et al. | 224/239 |
| 5,180,303 | 1/1993 | Hornburg et al. . | |
| 5,188,800 | 2/1993 | Green, Jr. et al. . | |
| 5,197,881 | 3/1993 | Chalifoux . | |
| 5,205,745 | 4/1993 | Kamiya et al. . | |
| 5,209,659 | 5/1993 | Friedman et al. . | |
| 5,254,005 | 10/1993 | Zuest . | |
| 5,254,314 | 10/1993 | Yu et al. | 422/102 |
| 5,269,685 | 12/1993 | Jorneus et al. . | |
| 5,270,011 | 12/1993 | Altherr . | |
| 5,281,140 | 1/1994 | Niznick . | |
| 5,282,746 | 2/1994 | Sellers et al. . | |
| 5,295,599 | 3/1994 | Smith | 215/204 |
| 5,297,963 | 3/1994 | Daftary . | |
| 5,312,254 | 5/1994 | Rosenlicht . | |
| 5,312,256 | 5/1994 | Scortecci . | |
| 5,324,199 | 6/1994 | Branemark . | |
| 5,362,235 | 11/1994 | Daftary . | |
| 5,364,268 | 11/1994 | Lazzara et al. . | |
| 5,366,374 | 11/1994 | Vlassis . | |
| 5,368,160 | 11/1994 | Leuschen . | |
| 5,415,545 | 5/1995 | Shaw . | |
| 5,431,567 | 7/1995 | Daftary . | |
| 5,435,172 | 7/1995 | O'Brien . | |
| 5,449,291 | 9/1995 | Lueschen et al. . | |
| 5,484,285 | 1/1996 | Morgan et al. . | |
| 5,538,428 | 7/1996 | Staubli . | |
| 5,582,299 | 12/1996 | Lazzara et al. . | |
| 5,591,029 | 1/1997 | Zuest . | |
| 5,622,500 | 4/1997 | Niznick . | |
| 5,667,094 | 9/1997 | Rapchak et al. . | |
| 5,695,336 | 12/1997 | Lazzara et al. . | |
| 5,702,346 | 12/1997 | Lazzara et al. . | |
| 5,709,547 | 1/1998 | Lazzara et al. . | |
| 5,711,468 | 1/1998 | Shoemaker . | |
| 5,857,600 | 1/1999 | Akutsu | 224/240 |

VIAL FOR DENTAL IMPLANT DELIVERY SYSTEM

BACKGROUND OF THE INVENTION

Dental implants are typically packaged and shipped in a package or implant delivery system. The delivery system and accompanying packaging maintain the implant in a sterile environment and typically include a vial housing an implant, a driver mount, and a healing cap In order to install an implant into the patient's jawbone, a sterile surgical field is prepared near the patient. Then, an implant site is prepared in the jawbone using conventional surgical procedures. Typically, an incision is made along the gingival tissue at the implant site, and a cylindrical bore is drilled into the bone. The vial is then positioned on the sterile surgical field, and the vial's lid is removed to expose the implant and driver mount. Next, a driving tool, such as a motorized dental hand-piece, is connected with an adapter to the end of the driver mount. The implant and driver mount are removed from the vial, and the end of the implant is fit within the bore. The driver mount then drives the implant into position. Once the implant is fully seated, the driver is disconnected from the driver mount; and the driver mount is removed from the implant. The healing cap is then removed from the vial and fastened on top of the implant. Thereafter, the gingival tissue is sutured, and the implant remains within the bone for several months as osseointegration and healing occur. During a second surgical procedure, the implant is re-exposed, the healing cap is removed, and a dental prosthesis is affixed to the implant.

Prior dental implant delivery systems have numerous disadvantages. During a dental implantation procedure, the vial should be placed in a stable and secure position on the sterile surgical field to keep the vial from accidentally falling over. Often, the vial is secured within a separate compartment in the surgical tray. This additional compartment, however, adds to the overall size and cost of the surgical tray.

Further, an implant delivery system should not generate unwanted refuse or secondary waste. This waste clutters the sterile surgical field and adds disposal time during the implantation procedure. Prior vials have a removable lid that constitutes such waste. During a typical implantation procedure, the lid must be removed from the vial to allow access to the implant. This lid must then be disposed or placed on the sterile field.

Additionally, two hands are required to remove the lid from the vial. Typically, the lid is peeled off while one hand holds the vial and the other hand removes the lid. A lid that could be removed with a single hand would be easier to use and less cumbersome. A separate lid also involves increased manufacturing costs, including the cost of the lid itself and labor associated with fastening the lid to the vial.

The present invention solves the problems discussed with prior dental implant delivery systems and provides further advantages.

SUMMARY OF THE INVENTION

The present invention is directed toward an improved vial for a dental implant delivery system. The vial has a clip formed on one side. This clip allows the vial to be securely fastened to the perimeter of a surgical tray. A separate compartment in the surgical tray for holding the vial is not required. Thus, the overall size and cost of the tray is reduced.

Additionally, the vial includes a lid that always remains attached to the vial itself. The lid is connected to a flexible arm that in turn connects to the body of the vial. When the lid is removed to expose the implant, the arm biases the lid away from the body of the vial. As such, the lid does not constitute extra refuse or secondary waste.

Further yet, the vial includes a lid that can be opened with one hand. When the sides of the vial are squeezed, the lid pops off the top of the vial.

The invention, accordingly, comprises the apparatus and method possessing the construction, combination of elements, and arrangement of parts that are exemplified in the following detailed description. For a fuller understanding of the nature and objects of the invention, reference should be made to the following detailed description taken in connection with the accompanying drawings.

DETAILED DESCRIPTION OF THE PREFERRED EMBODIMENTS

Figure 1:
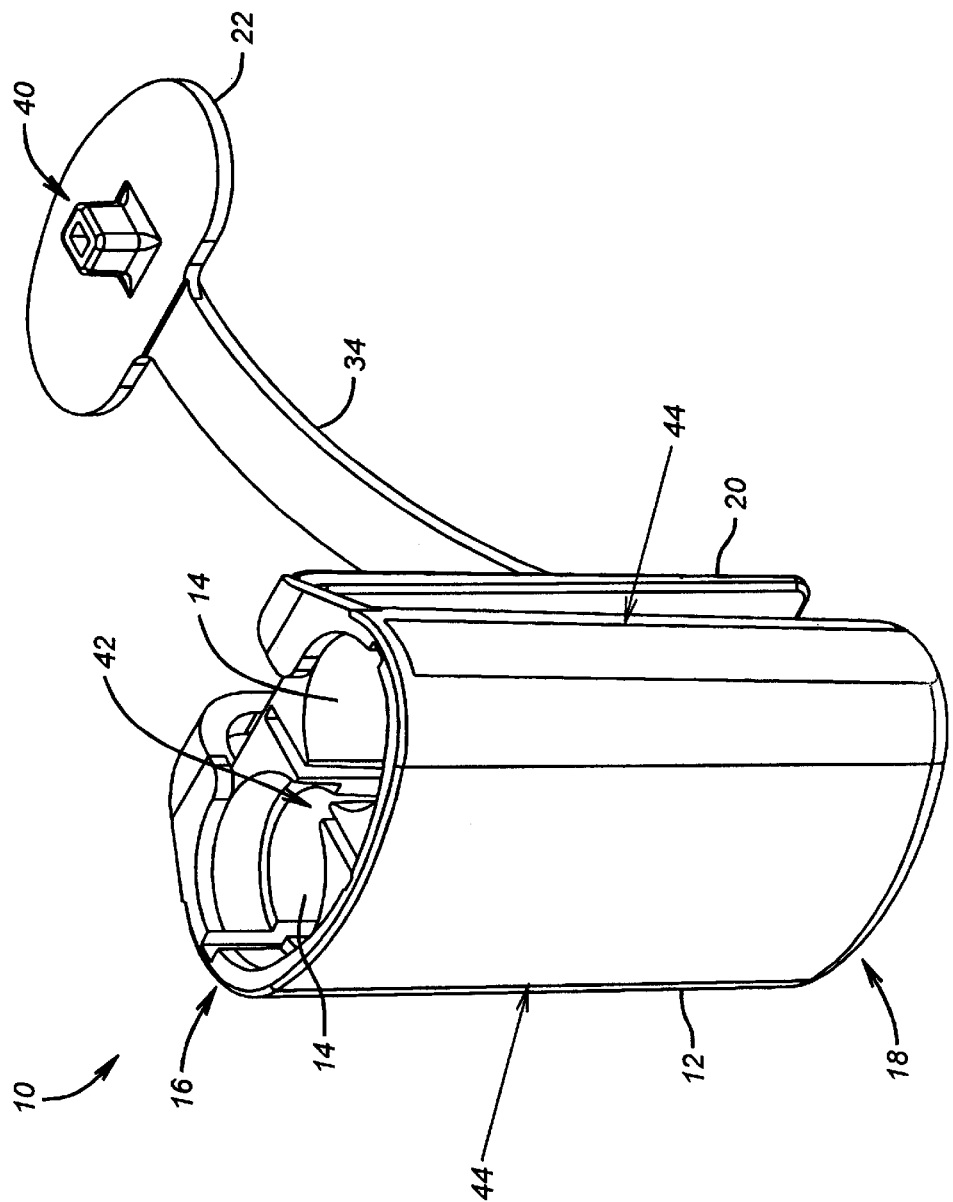
FIG. 1 is a perspective view of a vial for a dental implant delivery system.

FIG. 1 depicts a vial 10 for a dental implant delivery system. Vial 10 includes a body 12 having two cavities 14 extending from a top portion 16 toward a bottom portion 18. Cavities 14 have an elongated cylindrical configuration and are used to house dental components (not shown), such as an implant, driver mount, and healing cap.

The body may have various configurations, but preferably has an ergonomic design suited to be handled during a dental implant procedure. FIG. 1 illustrates such a design in which body 12 has a somewhat elongated elliptical configuration. It will be appreciated that the vial shown in FIG. 1 is exemplary, and other vial designs and configurations known to those skilled in the art also would be applicable with the present invention.

Figure 2:
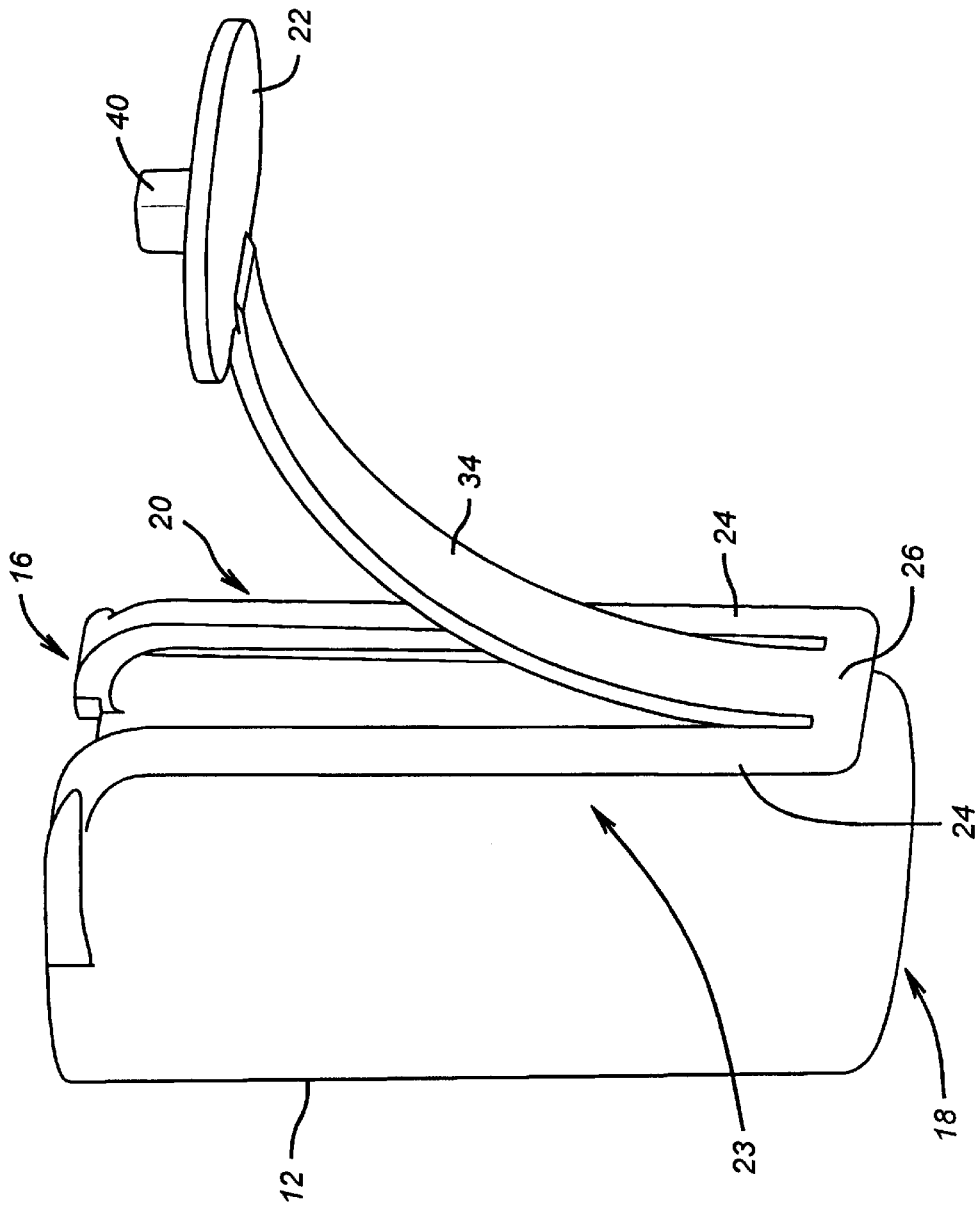
FIG. 2 is a rear-side view of the vial of FIG. 1.

Vial 10 further includes a clip 20 and a lid 22. FIG. 2 illustrates that clip 20 extends from top portion 16 along a backside 23. The clip connects to the body at the top portion and generally extends substantially to the vicinity of the bottom portion. The clip is formed from two arms 24 that extend generally parallel along the backside. These arms join at location 26 near the bottom portion.

Although the clip is formed having two connected arms, the clip could be formed with other configurations as well. For example, the clip could be formed as a single, wider arm that extends along the backside of the body. Additionally, the configuration of the clip may change by altering its width, length, or thickness.

Figure 3:
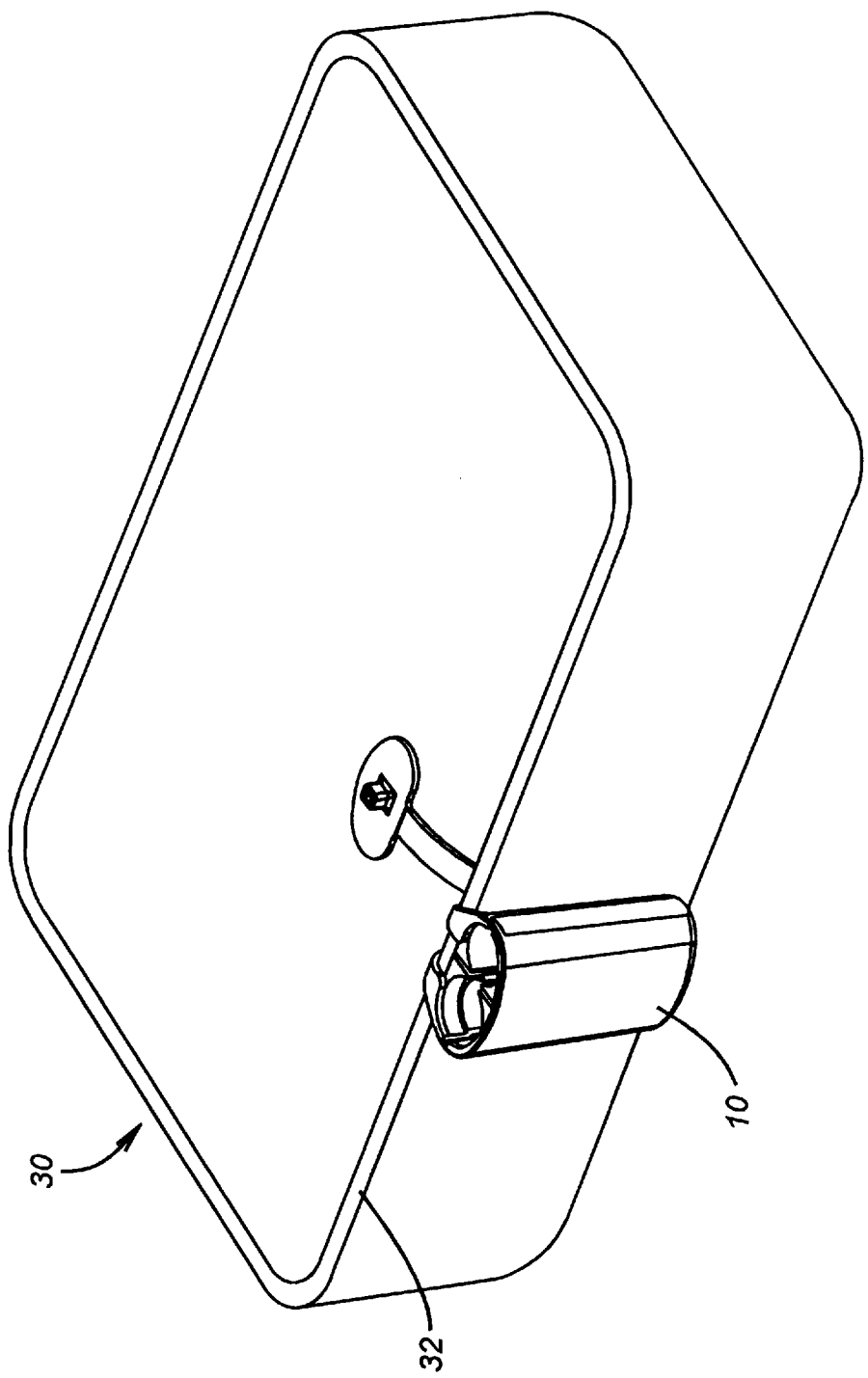
FIG. 3 is the vial of the present invention attached to a surgical tray.

The purpose of the clip is to securely attach and support the vial. FIG. 3 shows vial 10 attached to the periphery of a dental surgical tray 30. The clip attaches to an outer wall 32 of the tray. As such, a separate compartment in the tray for the vial is not necessary. The clip holds and supports the vial on the tray.

The clip is universal in that it may attach to a wide range of devices, such as a tray, kit, bowl, or other surface. Further, the clip may be flexible to enable it to connect to components with various thicknesses and configurations.

Turning back to FIG. 2, lid 22 is attached to body 12. A long flexible arm 34 extends from the lid to the body. In the figure, arm 34 connects to clip 20; however, the arm could alternatively connect directly to body 12.

One advantage of the present invention is that even after the lid is removed from the top portion, the lid remains attached to the body. As such, no refuse or secondary waste is generated when the vial is opened.

Lid 22 fits onto top portion 16 to cover cavities 14. The connection between the lid and the top portion is sufficient to seal the cavities and maintain them in a sterile environment. In alternative embodiments, the lid may only cover the cavities and not seal them.

Figure 4:
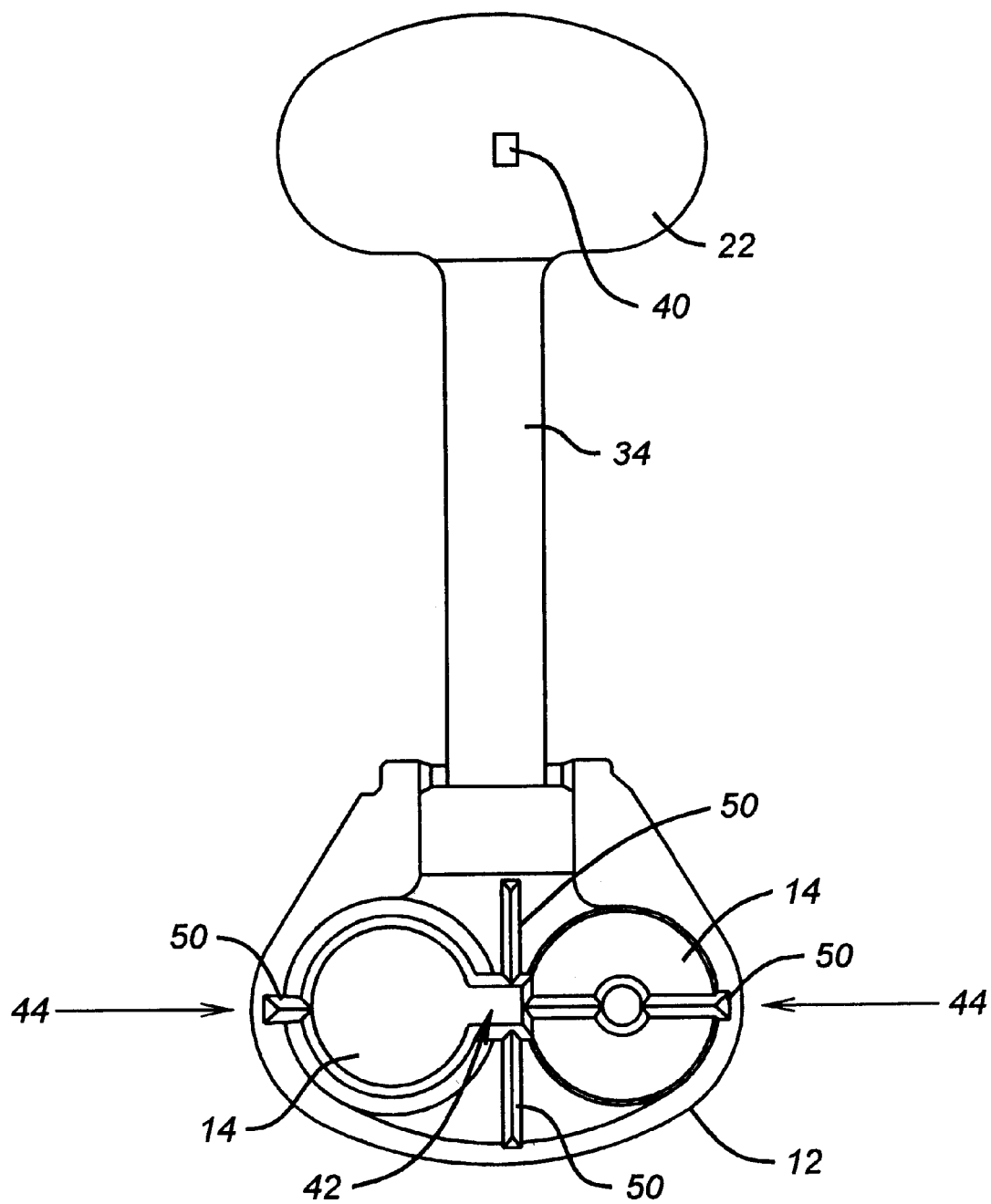
FIG. 4 is top view of the vial of FIG. 1.

Another aspect of the present invention is the release mechanism for the lid. Turning to FIGS. 1 and 4, lid 22 includes a boss or projection 40. The boss extends outwardly from a surface of the lid and is shaped in a rectangular configuration.

Top portion 16 of body 12 includes a recess 42. This recess is formed in a rectangular configuration corresponding to the shape of the projection. Recess 42 serves as a socket to receive and engage projection 40. When projection 40 is positioned within recess 42, lid 22 is secured to body 12, and cavities 14 are covered and secured.

When the lid is in a closed position and secured to top portion 16, the lid may be removed from body 12 with the action of a single hand. In particular, when compressive forces 44 (such as those applied when the body is squeezed with a hand) are applied to the sides of body 12, the lid releases from the top portion.

These compressive forces 44 slightly deform the body and in turn slightly deform recess 42, and in fact enlarge the recess. This enlargement is sufficient to remove the frictional engagement between the projection 40 and recess 42 and allow the projection to disengage from the recess. As the lid disengages from the body, flexible arm 34 biases the lid upwardly and away from top portion 16. The arm thus functions as a spring and automatically moves the lid away from the body. FIG. 1 illustrates the lid in an unbiased position away from the body.

It will be appreciated that the engagement between projection 40 and body 12 may have other mechanical configurations besides a frictional engagement. Such configurations include, for example, a hook or barb connection.

As shown in FIGS. 1 and 4, the body may have a series of slits or grooves 50. These grooves increase the flexibility and consequently the deformation of the body when the compressive forces are applied. The grooves, geometry of the vial, and material of the vial should be selected to enable the squeezing action of a hand to apply the necessary compressive forces to remove the lid from the body. The width, depth, placement, and number of these grooves will vary and depend on, for example, the configuration of the body and material used. In the preferred embodiment, the entire vial is made a semi-rigid polymer, such as polypropylene or polyurethane.

Since certain changes may be made in the above-described apparatus and method without departing from the scope of the invention herein involved, all matter contained in the description or shown in the accompanying drawings shall be interpreted as illustrative and not in a limiting sense.

What is claimed is:

1. A vial for housing a dental implant, comprising:

a body having a cavity extending from a top portion toward a bottom portion;

a lid for covering said cavity, said lid including a projection extending outwardly from a surface;

a socket formed within said top portion for engaging said projection; and said socket being deformed to release said projection when said lid covers said cavity and a compressive force is applied to said body.

2. The vial of claim 1 in which said body is formed from a flexible material.

3. The vial of claim 2 in which said material is a polymer such as polypropylene or polyurethane.

4. The vial of claim 1 in which:

said body includes a front, back, and two sides; and said compressive force enlarges said socket when applied to said two sides.

5. The vial of claim 1 in which:

said lid is in a closed position covering said cavity when said projection engages said socket;

said lid is in an open position uncovering said cavity when said projection disengages from said socket; and said lid moves from said closed position to said open position when said compressive force is applied to said body.

6. The vial of claim 5 in which:

said body includes a flexible arm that attaches at one end to said body and at another end to said lid; and said arm moves said lid away from said body in said open position.

7. A method for removing a lid from a vial for a dental implant delivery system, comprising the steps of:

providing a vial having: a body with a top portion and an internal cavity, a socket formed at said top portion, a lid covering said cavity and having a projection engaged within said socket, and a flexible arm extending between said lid and said body;

squeezing said body to deform said socket and disengage said projection; and biasing said lid with said flexible arm to move said lid away from said top portion.

* * * * *